(12) United States Patent
Diau et al.

(10) Patent No.: US 8,664,393 B2
(45) Date of Patent: Mar. 4, 2014

(54) RUTHENIUM COMPLEX-BASED PHOTOSENSITIZER DYES FOR DYE-SENSITIZED SOLAR CELLS

(75) Inventors: Eric Wei-Guang Diau, Hsinchu County (TW); Wei-Kai Huang, New Taipei (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/447,135

(22) Filed: Apr. 13, 2012

(65) Prior Publication Data

US 2012/0296086 A1    Nov. 22, 2012

(30) Foreign Application Priority Data

May 16, 2011  (TW) .............................. 100117109 A

(51) Int. Cl.
*C07F 15/00*   (2006.01)
*H01L 31/042*  (2006.01)

(52) U.S. Cl.
USPC ............................................. 546/2; 136/252

(58) Field of Classification Search
USPC ............................................. 546/2; 136/252
See application file for complete search history.

(56) References Cited

PUBLICATIONS

Sahin, C. et al.: The synthesis and characterization of 2-(2-pyridyl)benzimidazole heteroleptic ruthenium complex: Efficient sensitizer for molecular photovoltaics. Dyes and Pigments, vol. 84, pp. 88-94, 2010.*

Huang, W-K. et al.: Synthesis and electron-transfer properties of benzimidazole-functionalized ruthenium complexes for highly dye-sensitized solar cells. Chem. Commun. vol. 46, pp. 8992-8994, 2010.*

* cited by examiner

*Primary Examiner* — Charanjit Aulakh
(74) *Attorney, Agent, or Firm* — Muncy, Geissler, Olds & Lowe, P.C.

(57) ABSTRACT

This invention relates to ruthenium complex-based photosensitizer dyes for dye-sensitized solar cells, which have a general structural formula represented by formula (I).

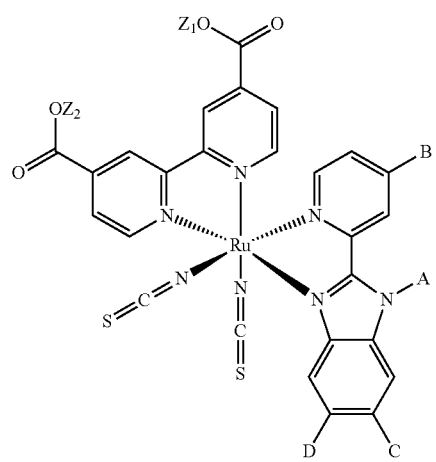

formula (I)

9 Claims, 1 Drawing Sheet

RUTHENIUM COMPLEX-BASED PHOTOSENSITIZER DYES FOR DYE-SENSITIZED SOLAR CELLS

CLAIM OF PRIORITY

This application claims the priority benefit of Taiwanese Application Serial Number 100117109, filed on May 16, 2011. All disclosure of the Taiwanese application is incorporated herein by reference.

BACKGROUND OF THE INVENTION

A. Field of this Invention

This invention relates to a type of ruthenium complex photosensitizer dyes. More specifically, this invention relates to the type of ruthenium complex photosensitizer dyes for dye-sensitized solar cells.

B. Description of the Relevant Art

In conventional dye-sensitized solar cells, N719 photosensitizer dye is usually employed. However, since the N719 photosensitizer dye has a relatively large molecular structure, the sun light is not easy to be absorbed onto thin titanium dioxide photoanodes of solar cells, leading to low photoelectric current. Therefore, the conventional dye-sensitized solar cells employing the N719 photosensitizer dye have low current density, and the overall solar elements have low efficiency. In this situation, in order to improve photoelectric current, the number of layers of the titanium dioxide photoanode element must be increased, which, in turn, increases the cost for manufacturing.

SUMMARY OF THE INVENTION

This invention relates to a type of ruthenium complex photosensitizer dyes for dye-sensitized solar cells, which are represented by the general formula (I):

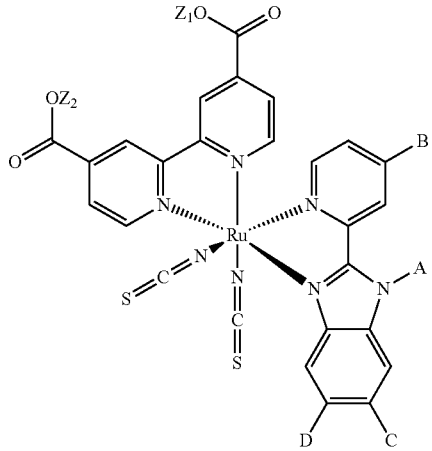

formula (I)

where $Z_1$ and $Z_2$ individually represent H, Li, Na, or tetra-alkyl ammonium group represented by the formula (a),

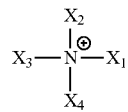

(a)

where $X_1$ to $X_4$ individually represent $C_mH_{2m+1}$ (m is an integer from 1 to 6), In formula (I), A is one of the followings: H or $C_mH_{2m+1}$ (m is an integer from 1 to 15), or $CH_2[OC_2H_4]_pOC_mH_{2m+1}$ (p is an integer from 1 to 30, m is an integer from 1 to 15);

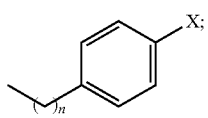
110

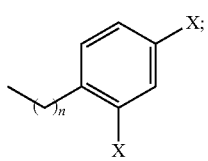
111

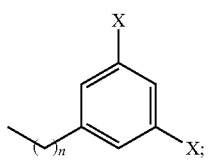
112

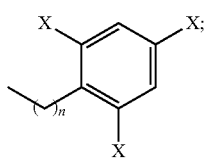
113

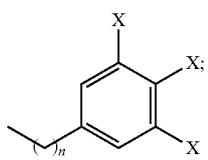
114

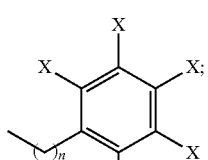
115

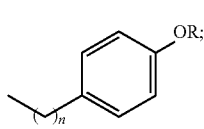
116

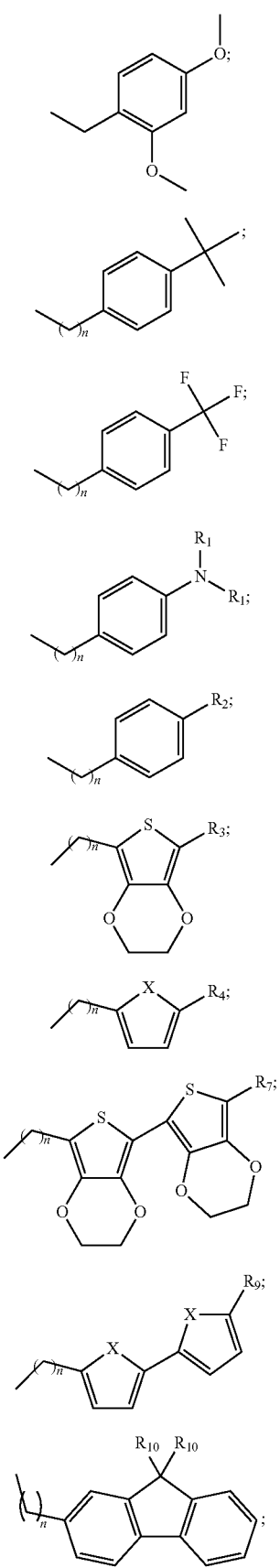
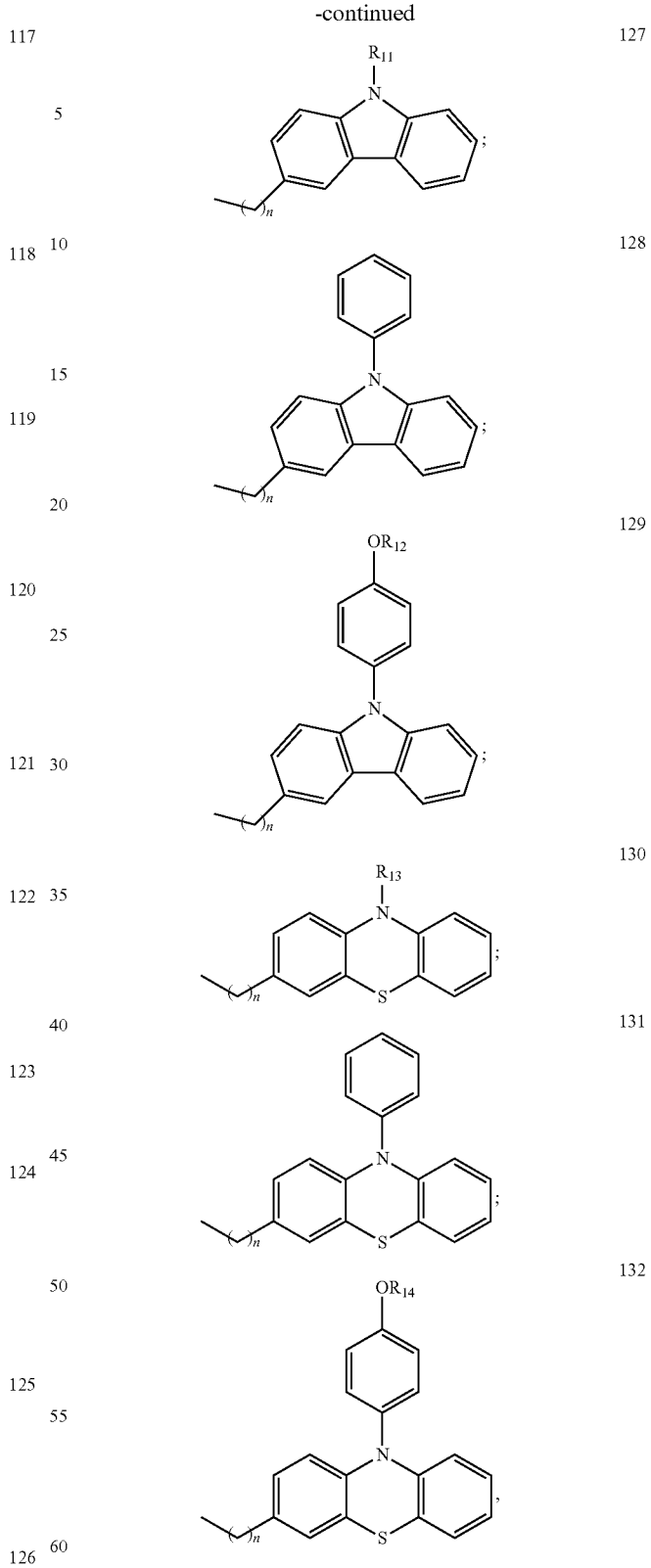
In formulae (110) to (132), n is zero or an integer from 1 to 15.
In formula (I), B, C, and D are individually selected from the followings: H, or $C_mH_{2m+1}$ (m is an integer from 1 to 15), or $CH_2[OC_2H_4]_pOC_mH_{2m+1}$ (p is an integer from 1 to 30, m is an integer from 1 to 15);

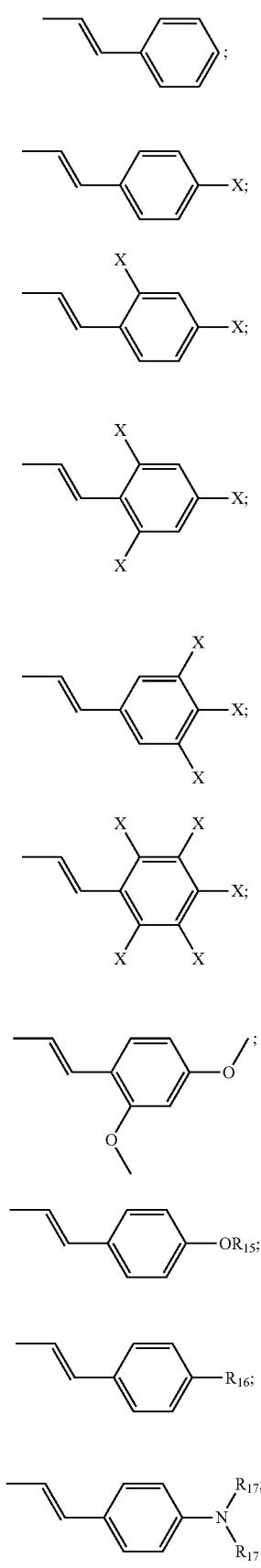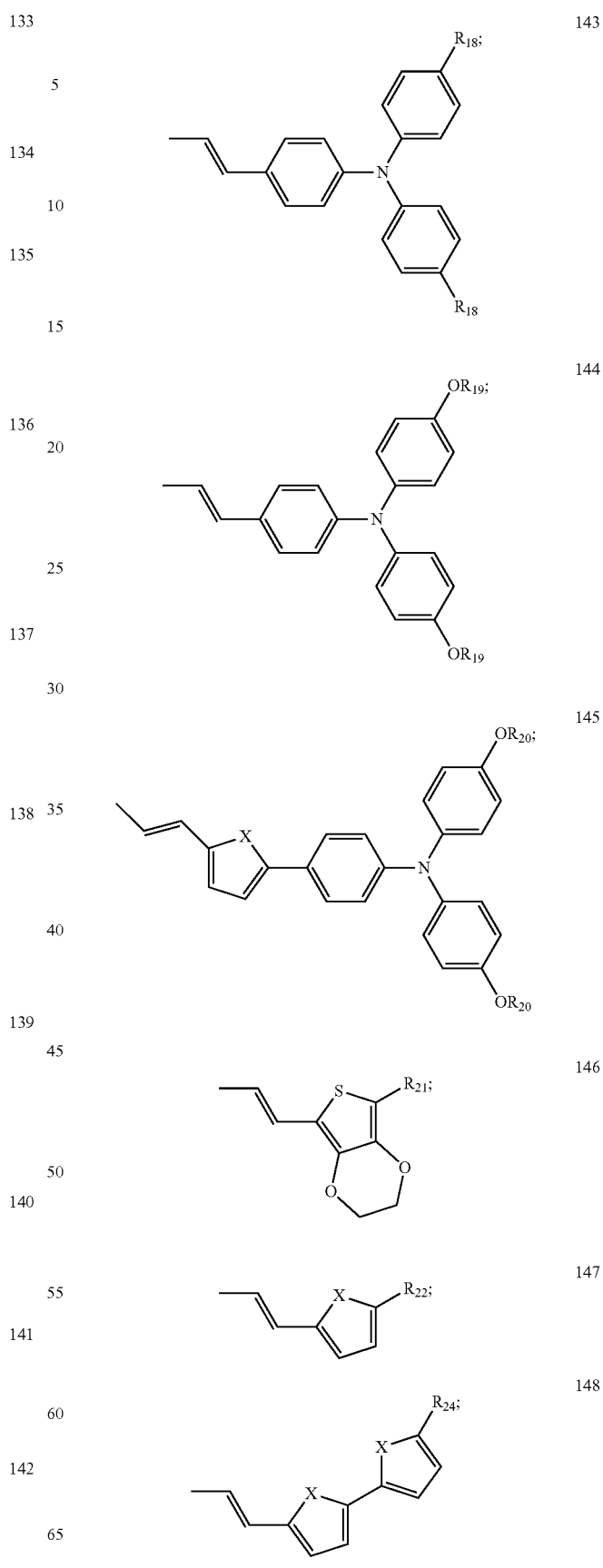

149 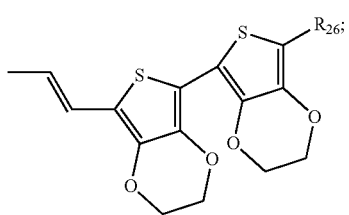
150 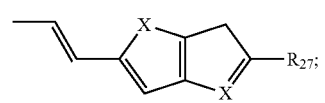
151 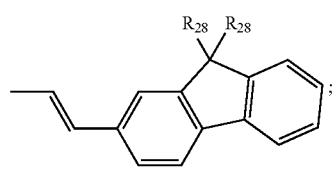
152 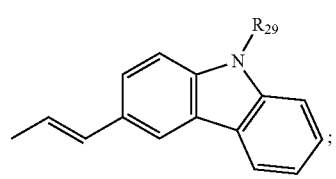
153 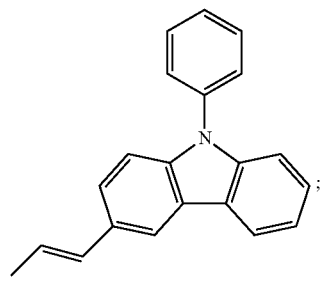
154 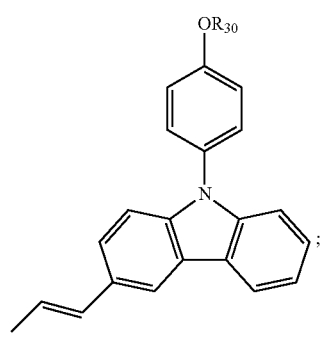
155 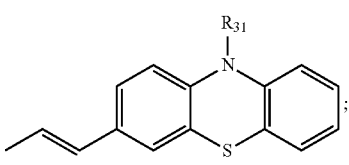
156 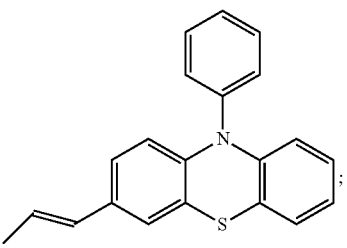
157 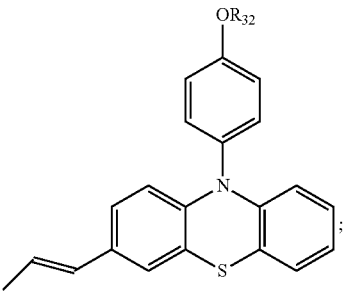
158 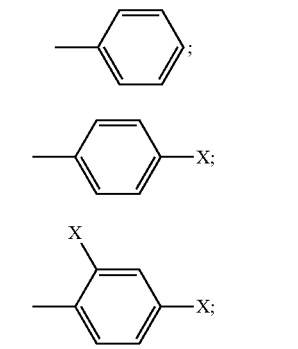
159 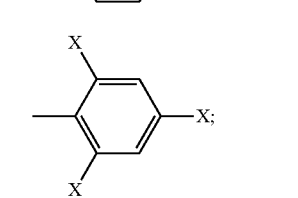
160 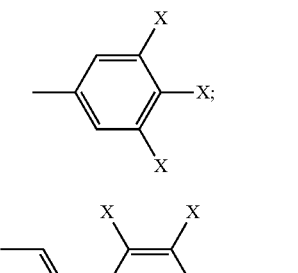
161 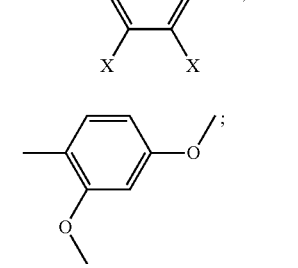
162 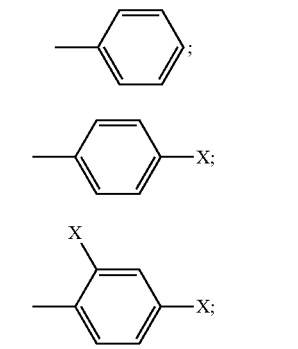
163 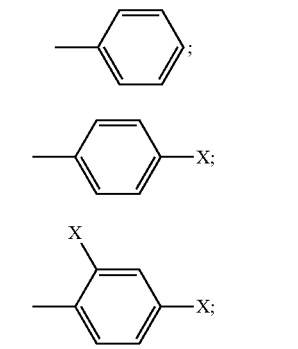
164 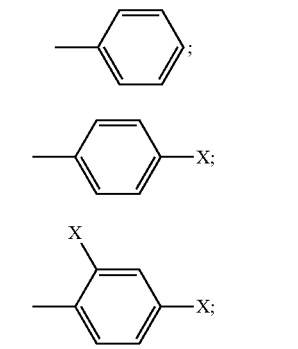

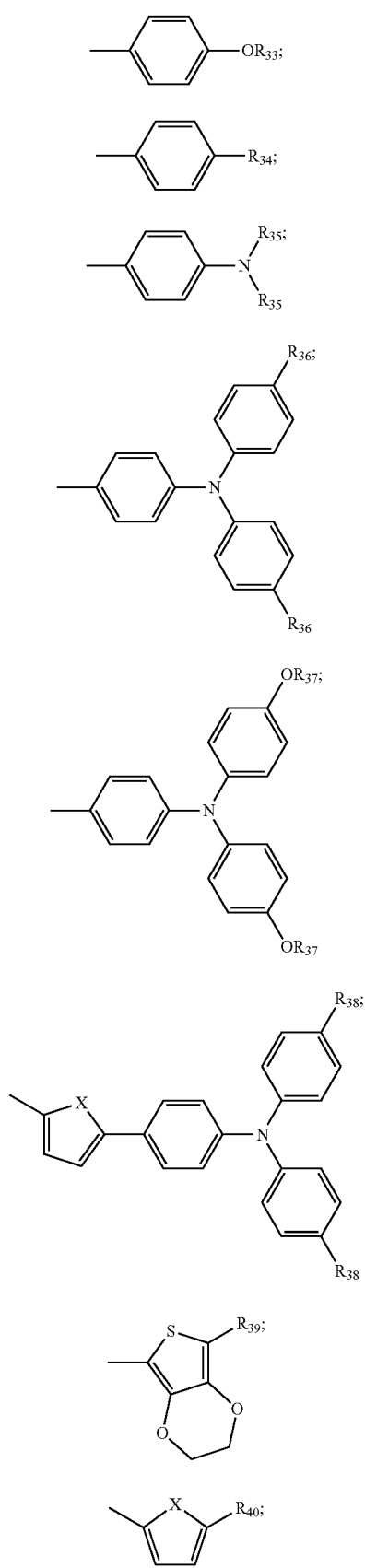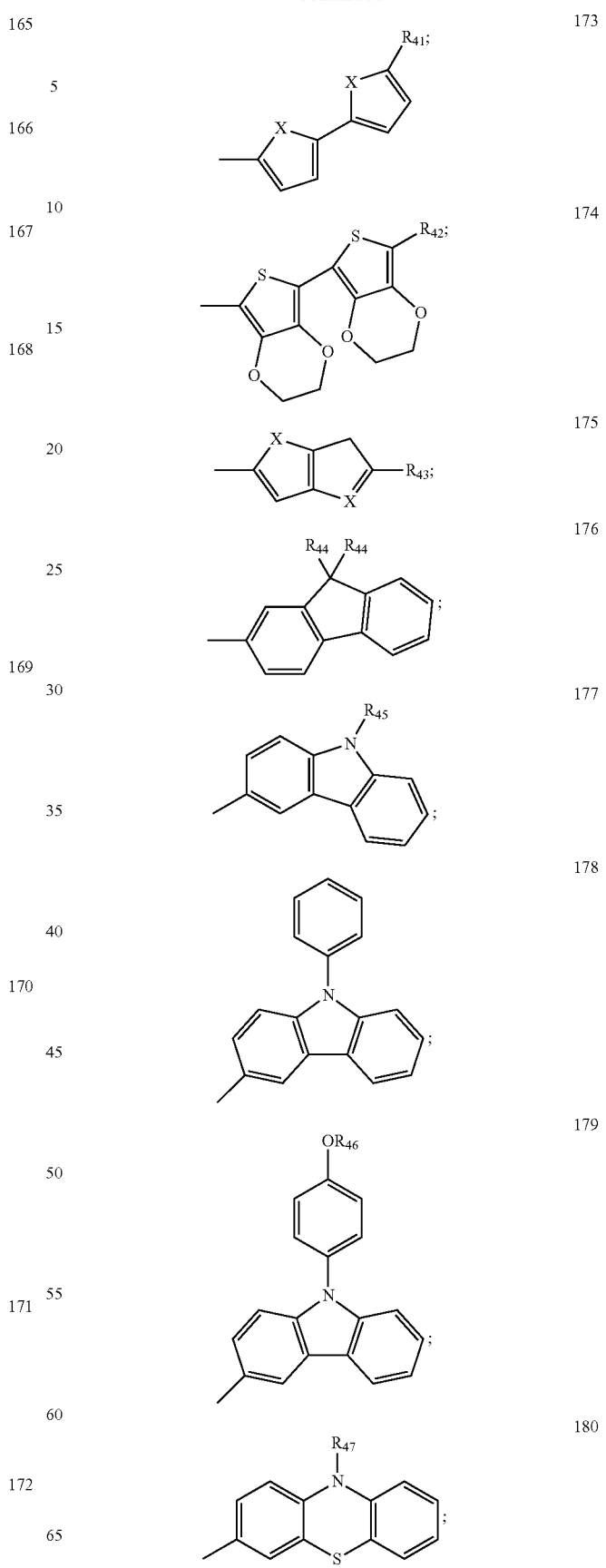

-continued

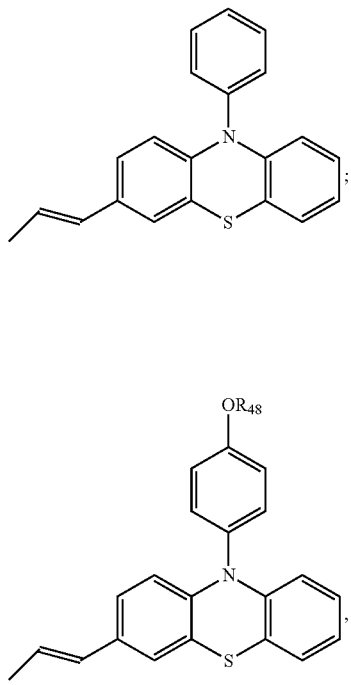

181

182

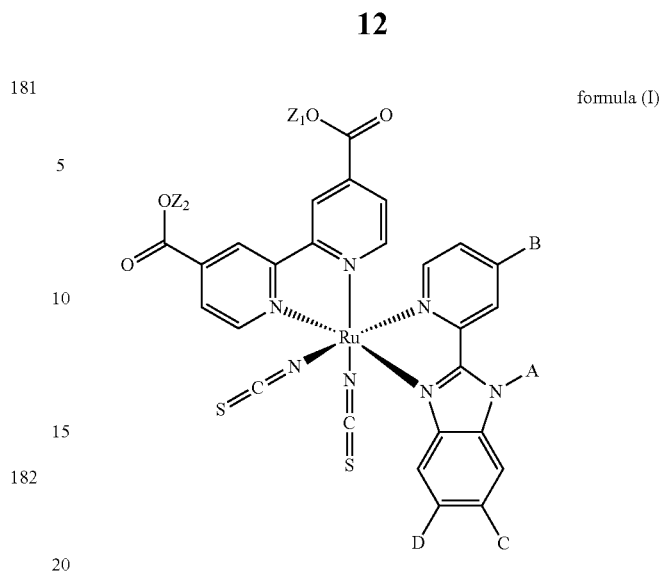

formula (I)

where $Z_1$ and $Z_2$ individually represent hydrogen atom (H), lithium (Li), sodium (Na), or tetra-alkyl ammonium group represented by the following formula (a), (a)

$$X_3-\overset{X_2}{\underset{X_4}{N^{\oplus}}}-X_1$$

where $X_1$ to $X_4$ individually represent $C_mH_{2m+1}$ (m is an integer from 1 to 6), In formula (I), A is one of the followings: H, or $C_mH_{2m+1}$ (m is an integer from 1 to 15), or $CH_2[OC_2H_4]_pOC_mH_{2m+1}$ (p is an integer from 1 to 30, m is an integer from 1 to 15);

where $R_3$, $R_4$, $R_7$, $R_9$, $R_{10}$, $R_{21}$, $R_{22}$, $R_{24}$, $R_{26}$, $R_{27}$, and $R_{39}$ to $R_{43}$ represent $C_mH_{2m+1}$ (m is zero or an integer from 1 to 15);

R, $R_{12}$ to $R_{15}$, $R_{19}$, $R_{28}$ to $R_{33}$, $R_{37}$, and $R_{44}$ to $R_{48}$ represent $C_mH_{2m+1}$ (m is an integer from 1 to 15);

$R_1$, $R_{11}$, $R_{17}$, and $R_{35}$ represent $C_mH_{2m+1}$ (m is an integer from 1 to 15) or phenyl;

$R_2$, $R_{16}$, and $R_{34}$ represent $CH_2[OC_2H_4]_pOC_mH_{2m+1}$ (p is an integer from 1 to 30, m is an integer from 1 to 15);

$R_{18}$, $R_{20}$, $R_{36}$, and $R_{38}$ represent $CH_2[OC_2H_4]_pOC_mH_{2m+1}$ or $C_mH_{2m+1}$ (p is an integer from 1 to 30, m is an integer from 1 to 15).

In formulae 123, 125, 147, 148, 150, 170, 172, 173 and 175, X represents Se, S or O, In formulae 110 to 115 and 134 to 138, X represents F, Cl, Br, I or $C_mH_{2m+1}$ (m is an integer from 1 to 15).

Other aspects and advantages of this invention will become apparent from the following detailed descriptions.

DETAILED DESCRIPTION OF THE PREFERRED EMBODIMENTS

Figure 1:
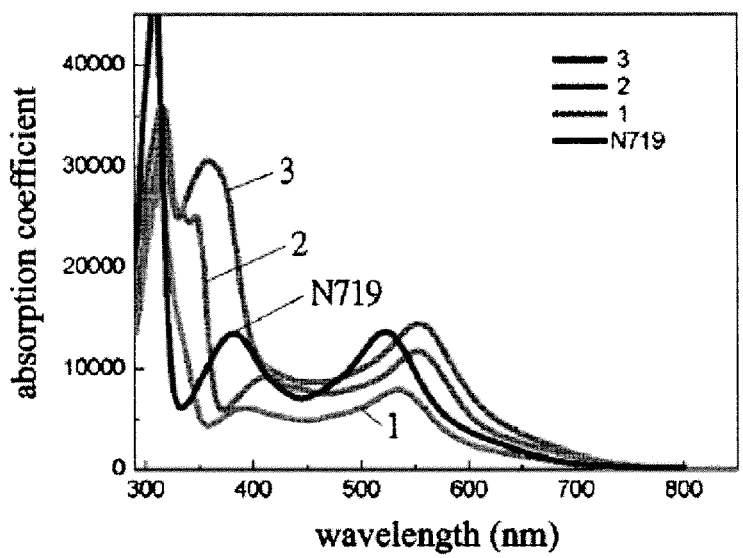
FIG. 1 shows the UV-visible spectra of ruthenium complex photosensitizer dyes 1, 2 and 3 of this invention and conventional N719 dye.

According to one embodiment of this invention, a ruthenium complex photosens tizer dye is represented by the following general formula (I):

110

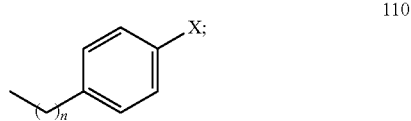
111

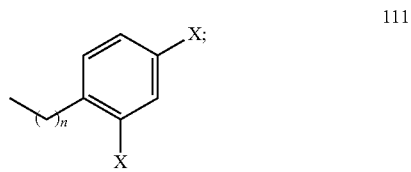
112

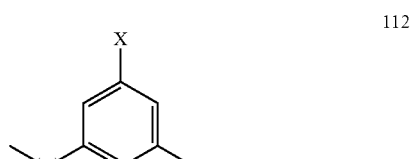
113

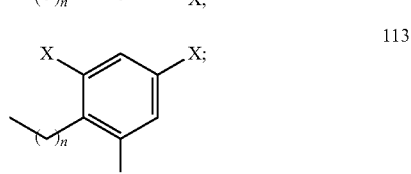

-continued
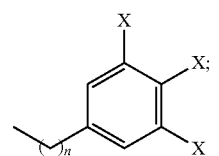
114
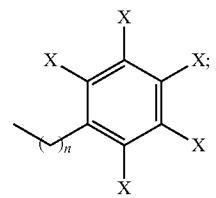
115
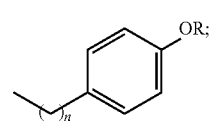
116
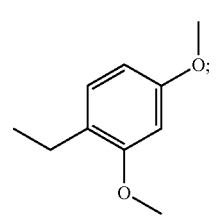
117
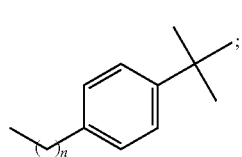
118
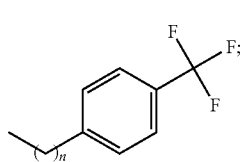
119
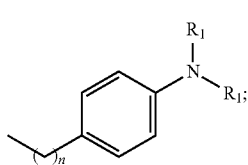
120
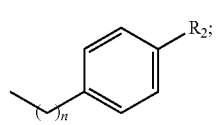
121
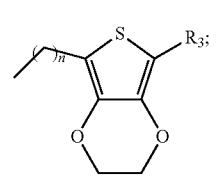
122
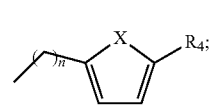
123
-continued
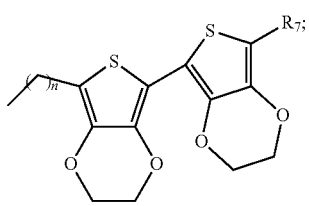
124
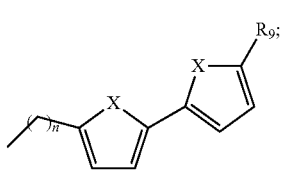
125
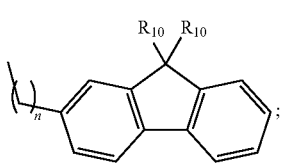
126
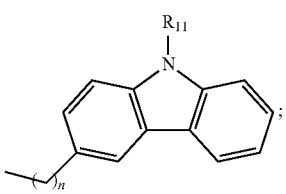
127
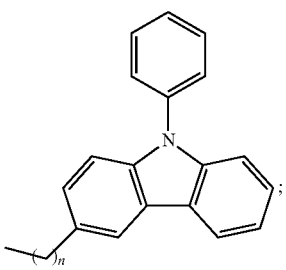
128
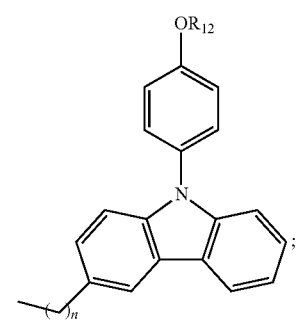
129
130

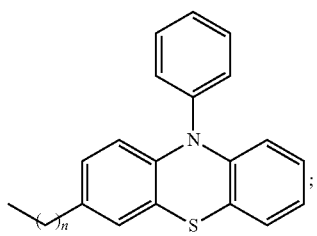
131
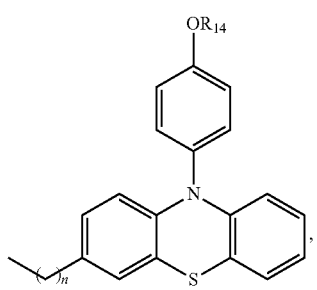
132
In the formulae (110) to (132), n is zero or an integer from 1 to 15,
In formula (I), B, C, and D are individually one of the followings: H, or $C_mH_{2m+1}$ (m is an integer from 1 to 15), or $CH_2[OC_2H_4]_pOC_mH_{2m+1}$ (p is an integer from 1 to 30, m is an integer from 1 to 15);
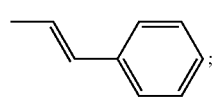
133
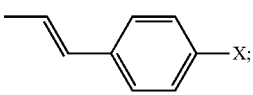
134
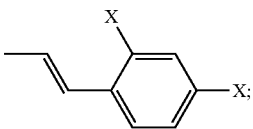
135
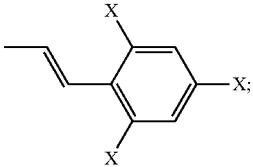
136
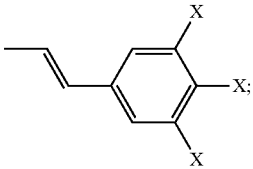
137
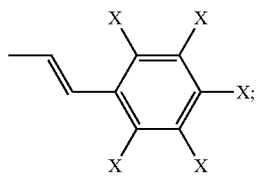
138
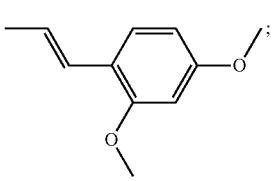
139
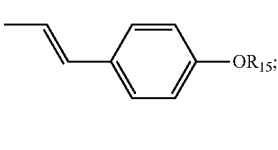
140
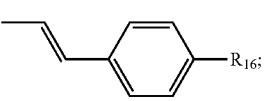
141
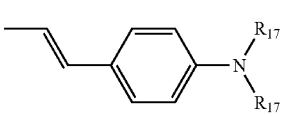
142
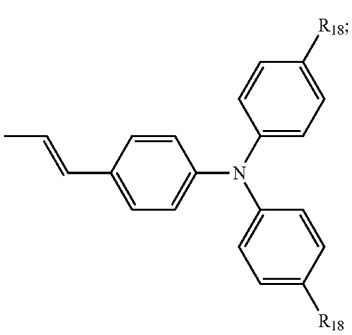
143
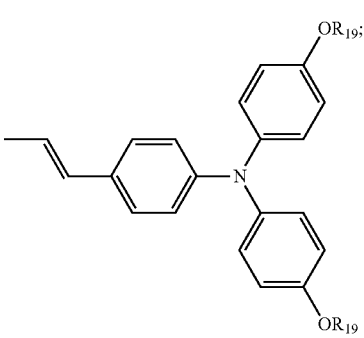
144

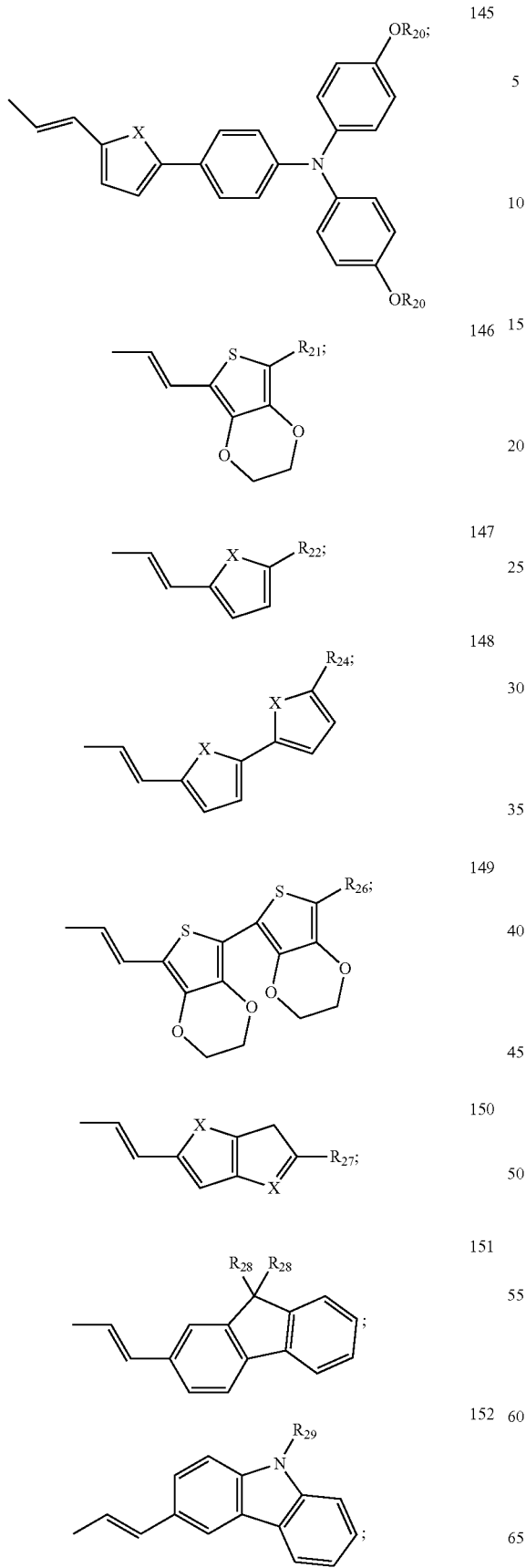
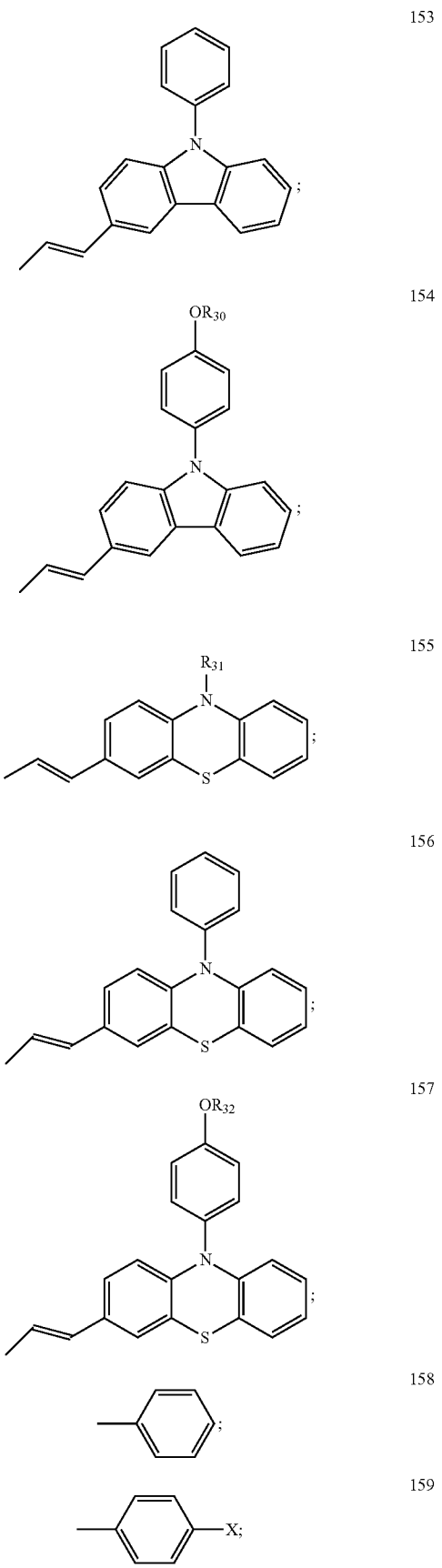

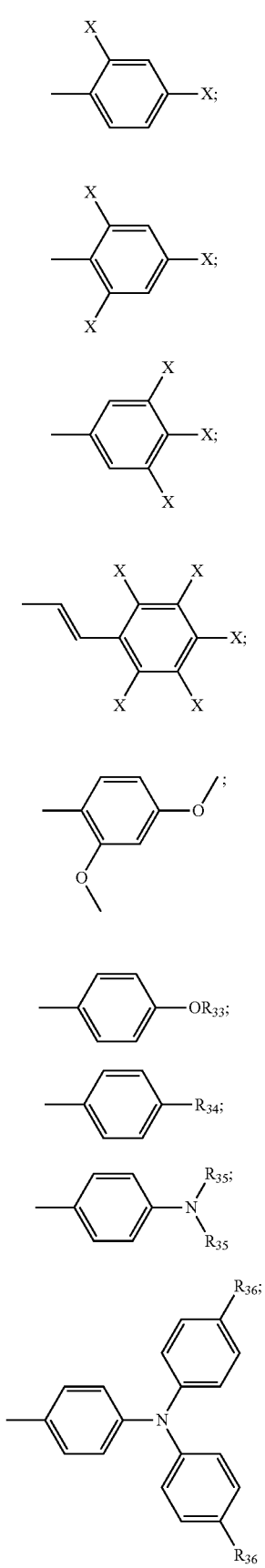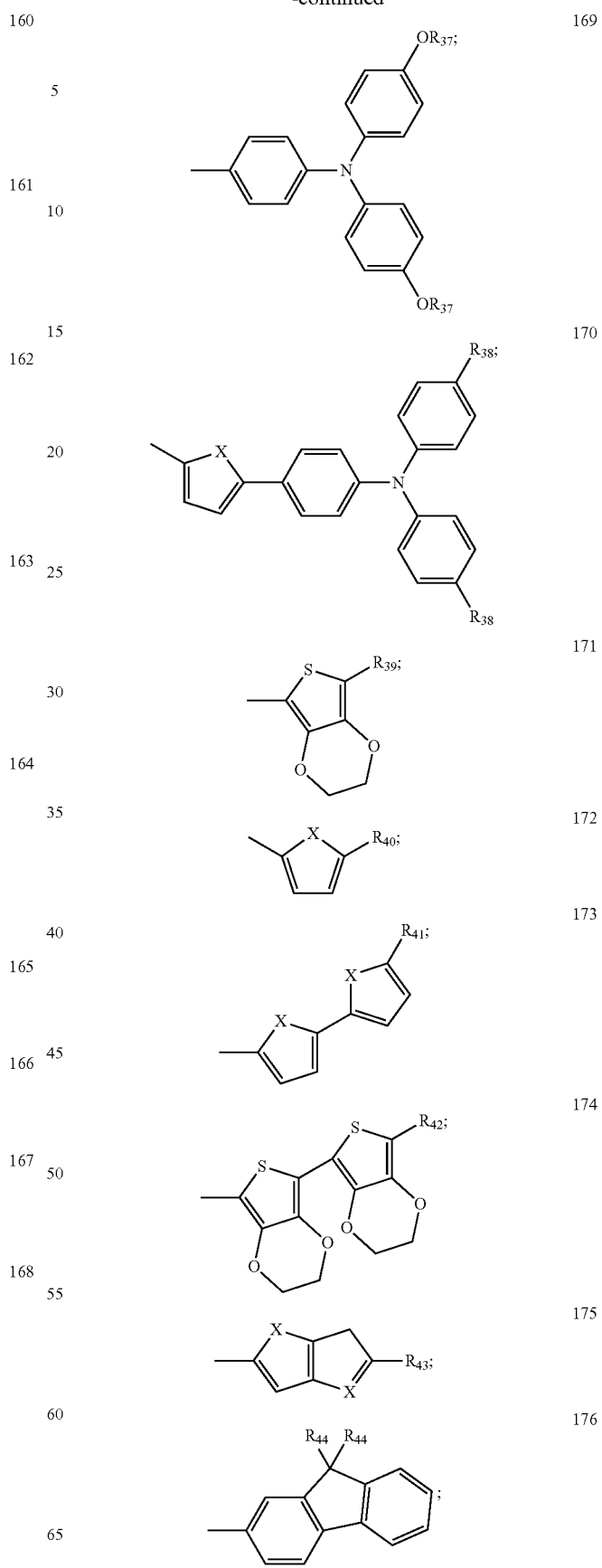

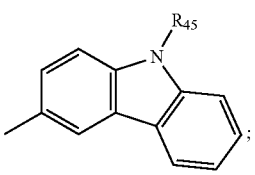
177

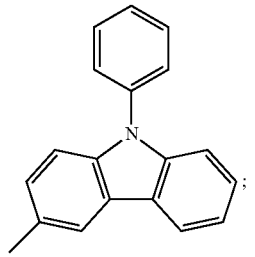
178

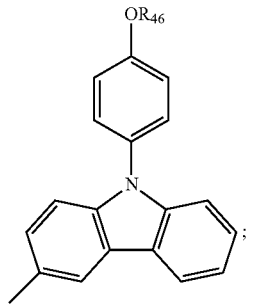
179

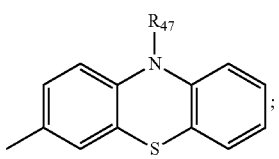
180

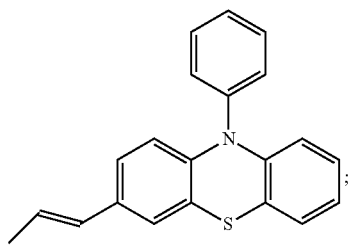
181

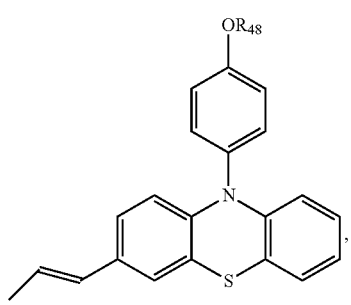
182 where $R_3$, $R_4$, $R_7$, $R_9$, $R_{10}$, $R_{21}$, $R_{22}$, $R_{24}$, $R_{26}$, $R_{27}$, and $R_{39}$ to $R_{43}$ represent $C_mH_{2m+1}$ (m is zero or an integer from 1 to 15);

R, $R_{12}$ to $R_{15}$, $R_{19}$, $R_{28}$ to $R_{33}$, $R_{37}$, and $R_{44}$ to $R_{48}$ represent $C_mH_{2m+1}$ (m is an integer from 1 to 15);

$R_1$, $R_{11}$, $R_{17}$, and $R_{35}$ represent $C_mH_{2m+1}$ (m is an integer from 1 to 15) or phenyl;

$R_2$, $R_{16}$, and $R_{34}$ represent $CH_2[OC_2H_4]_pOC_mH_{2m+1}$ (p is an integer from 1 to 30, m is an integer from 1 to 15);

$R_{18}$, $R_{20}$, $R_{36}$, and $R_{38}$ represent $CH_2[OC_2H_4]_pOC_mH_{2m+1}$ or $C_mH_{2m+1}$ (p is an integer from 1 to 30, m is an integer from 1 to 15).

In formulae 123, 125, 147, 148, 150, 170, 172, 173 and 175, X represents Se, S or O.

In formulae 110 to 115 and 134 to 138, X represents F, Cl, Br, I or $C_mH_{2m+1}$ (m is an integer from 1 to 15).

Several exemplary embodiments will be described below to illustrate the processes of synthesis of the ruthenium complex photosensitizer dyes 1, 2 and 3 of this invention. The structures of the ruthenium complex photosensitizer dyes 1, 2 and 3 are showed below. It must be understood that the exemplary embodiments should be regarded as illustrative rather than restrictive.

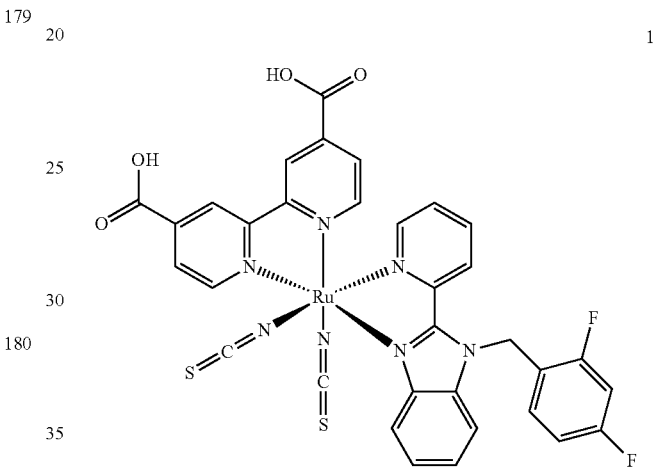
1

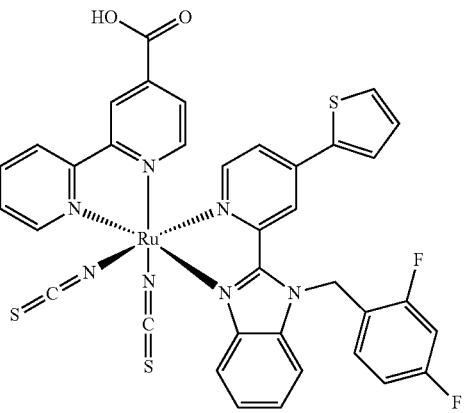
2

-continued

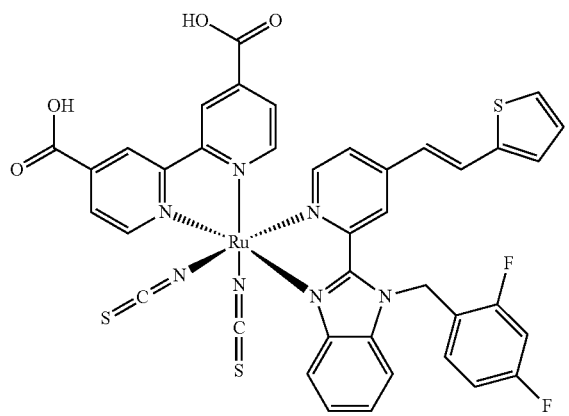

Embodiment Number One

1. The Synthesis of Ligands of Ruthenium Complex Photosensitizer Dye 1

Step 1

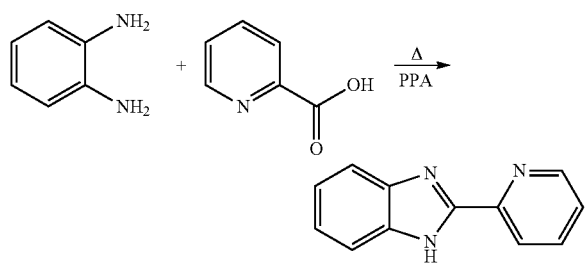

Put 20 mL of polyphosphoric acid (PPA) into a double-necked flask, stir and preheat the solution to about 90° C. Then, slowly add about 2.46 g (about 0.02 mol) of 2-picolinic acid into the double-necked flask, and keep stirring the mixture evenly for about 30 minutes. Afterwards add about 2.16 g (about 0.02 mol) of o-phenylenediamine, then raise temperature to about 150° C. and keep stirring evenly the mixture for about 4 hours. When the reaction ends, lower the temperature of the mixture to about 100° C. Then, carefully and rapidly pour the reactant into iced water, and neutralize the mixture to weak alkalinity (about pH 9) with 1M sodium hydroxide (NaOH) solution. A pinkish purple color solid product is precipitated now. The solid is filtered out by suction, then it is dried by heat and purified by column chromatograph using a hexane/ethyl acetate (EA) solution (1:2) as eluent. About 2.21 g of white color solid is obtained with the yield of about 56.7%. The white solid product is 2-(pyridin-2-yl)-1H-benzimidazole.

Step 2

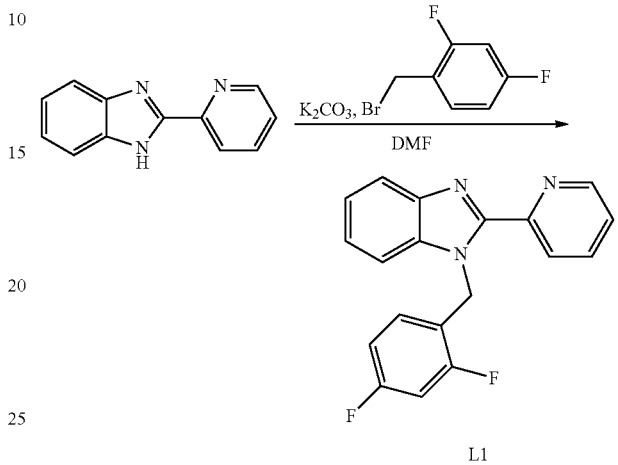

Mix about 0.195 g (about 1 mmol) of the white solid product obtained in Step 1, about 0.276 g (about 2 mmol) of K$_2$CO$_3$, and about 15 mL of N,N'-dimethylformamide (DMF) in a reaction vessel and keep stirring for about 10 minutes. Then, carefully inject about 0.385 mL (about 3 mmol) of 2,4-difluorobenzyl bromide into the mixture by a syringe and let the mixture react for about 3 hours at room temperature. When the reaction ends, pour the reactant into iced water and extract using EA. Then collect and dehydrate the organic layer using anhydrous sodium sulfate. After filtration and concentration, a yellow color viscous liquid is obtained. Then purify the yellow viscous liquid by column chromatograph using a hexane/EA solution (3:1) as eluent. Then, dry it by vacuum suction and collect about 0.242 g of beige-white color solid (i.e. the ligands L1). The yield is about 75.3%.

2. The Synthesis of Ruthenium Complex Photosensitizer Dye 1

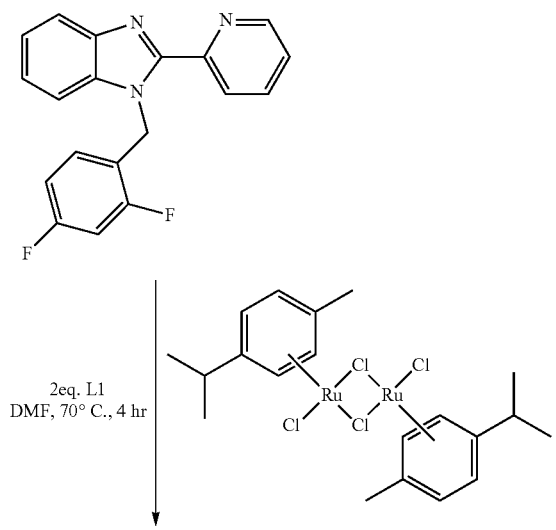

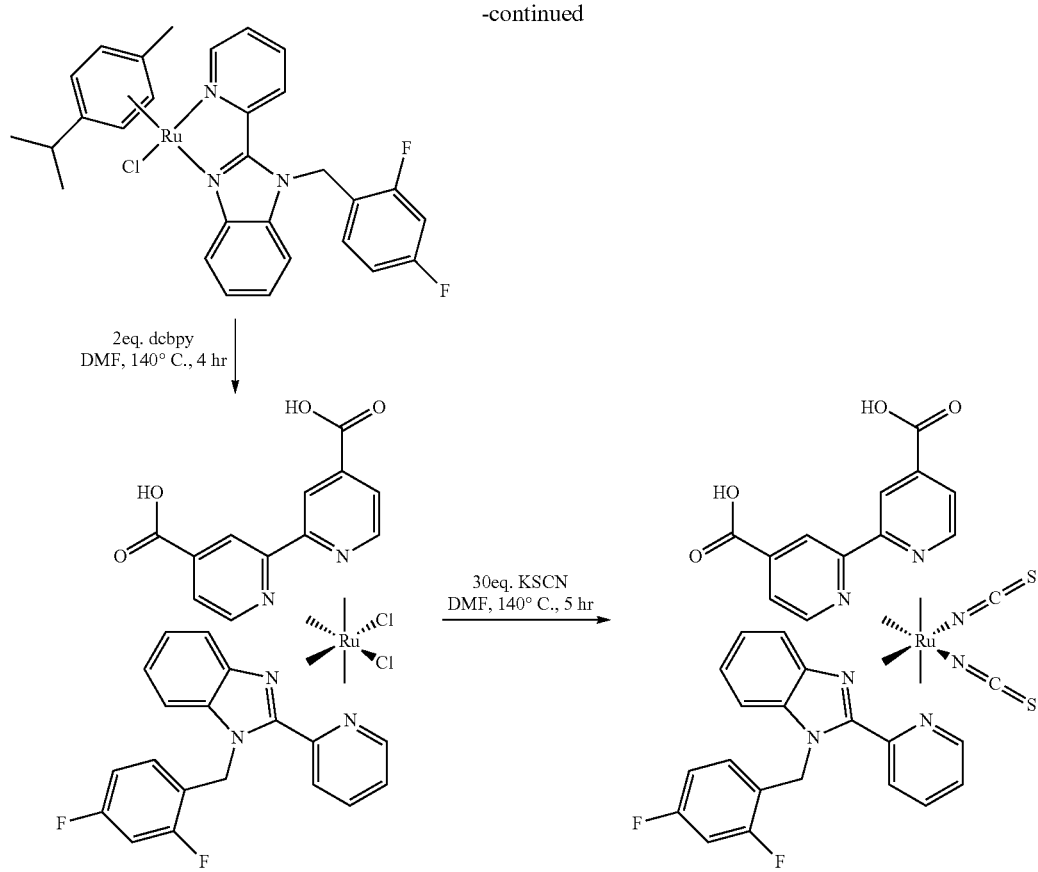

The steps of synthesis of ruthenium complex photosensitizer dye 1 are shown below.

(1) In the environment of DMF and argon (Ar), two equivalents of the ligand L1 (about 0.257 g, about 0.8 mmol) are reacted with one equivalent of [RuCl$_2$(p-cymene)]$_2$ (about 0.244 g, about 0.4 mmol) at a temperature of about 70° C. for about 4 hours to form [Ru(L1)(p-cymene)]Cl coordination from broken dichloride-bridged structure.

(2) Then, add two equivalents of 4,4'-dicarboxy-2,2'-bipyridine (dcbpy, L) (about 0.195 g, about 0.8 mmol) and raise the temperature to about 140° C. for reaction for about 4 hours, resulting in [Ru(L)(L1)(Cl)$_2$].

(3) Finally, add excess amount of potassium thiocyanate (KSCN) and let the mixture react at about 140° C. for about 5 hours. After that, remove residual DMF from the reaction vessel using a distillation apparatus and KSCN residuals by water (H$_2$O). After suction filtration, about 0.563 g of the ruthenium complex photosensitizer dye 1 is obtained. The yield is about 90%.

Embodiment Number Two

1. The Synthesis of Ligands of Ruthenium Complex Photosensitizer Dye 2

Step 1

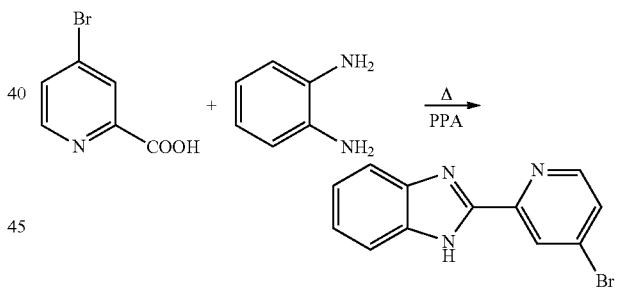

Put 20 mL of polyphosphoric acid (PPA) into a double-necked flask, stir and preheat to about 90° C. Then, slowly add about 2.00 g (about 0.02 mol) of 4-bromopyridine-2-carboxylic into the flask, and keep stirring the mixture evenly for about 30 minutes. Afterwards, add about 1.08 g (about 0.01 mol) of o-phenylenediamine and raise the temperature to about 150° C. and keep stirring the mixture evenly for about 4 hours. When the reaction ends, lower the temperature to about 100° C. Then, carefully and rapidly pour the reactant into iced water, and neutralize it to weak alkalinity (about pH 9) with 1M sodium hydroxide solution. A pinkish purple color solid product is precipitated. The solid product is filtered by suction and dried by heat, then purified by column chromatograph using a hexane/EA solution (1:3) as eluent. About 1.47 g of white color solid is obtained with the yield of about 53.8%. The white solid product is 2-(4-bromopyridine-2-yl)-1H-benzimidazole.

Step 2

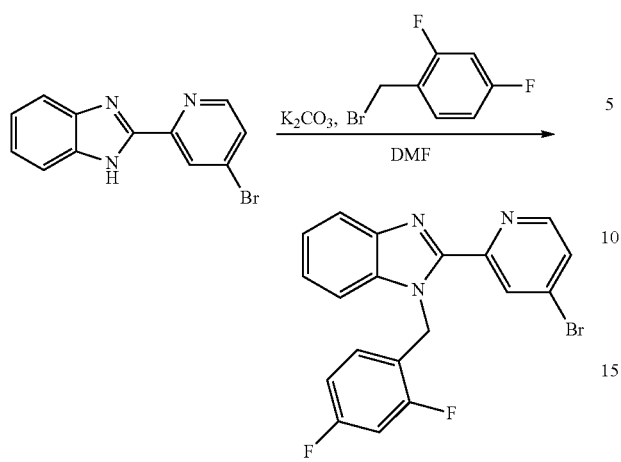

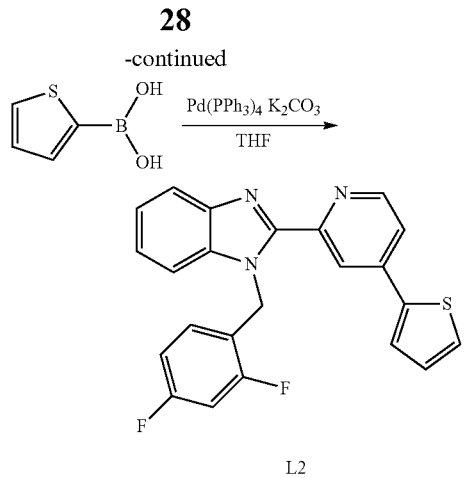

L2

Mix about 0.273 g (about 1 mmol) of the white solid product obtained in Step 1, about 0.276 g (about 2 mmol) of $K_2CO_3$, and about 15 mL of DMF in a reaction vessel and stir for about 10 minutes. Then, carefully inject about 0.385 mL (about 3 mmol) of 2,4-difluorobenzyl bromide into the mixture by a syringe and keep at room temperature for about 3 hours. When the reaction ends, pour the reactant into iced water and extract using EA. Collect the organic layer and dehydrate it using anhydrous sodium sulfate. After filtration and concentration, a yellow color viscous liquid is obtained. Then purify the yellow viscous liquid by column chromatograph using a hexane/EA solution (2:1) as eluent. Then, after vacuum suction, about 0.273 g of beige-white color solid is obtained with the yield of about 68.3%. The beige-white solid product is 1-(2,4-difluorobenzyl)-2-(4-bromopyridin-2-yl)-benzimidazole.

Step 3

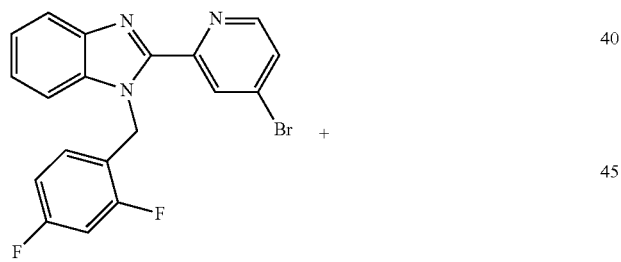

Mix about 0.24 g (about 0.6 mmol) of the beige-white solid product obtained in Step 2, about 0.092 g (about 0.72 mmol) of thiophen-2-yl-2-boronic acid, about 0.0462 g (about 0.04 mmol) of $Pd(PPh_3)_4$, and about 20 mL of tetrahydrofuran (THF) in a reaction vessel. In the environment of nitrogen gas, add about 2 mL of 2M $K_2CO_3$, then the mixture is heated and refluxed for about 8 hours. When the reaction ends, pour the reactant into iced water and extracte using $CH_2Cl_2$. Collect and dehydrate the organic layer using anhydrous magnesium sulfate. After filtration and concentration, a light yellow color viscous liquid is obtained. Purify the light yellow viscous liquid by column chromatograph using a hexane/EA solution (10:1) as eluent. Then, about 0.22 g of beige-white color solid (i.e. the ligands L2) is obtained with the yield of about 91%.

2. The Synthesis of Ruthenium Complex Photosensitizer Dye 2

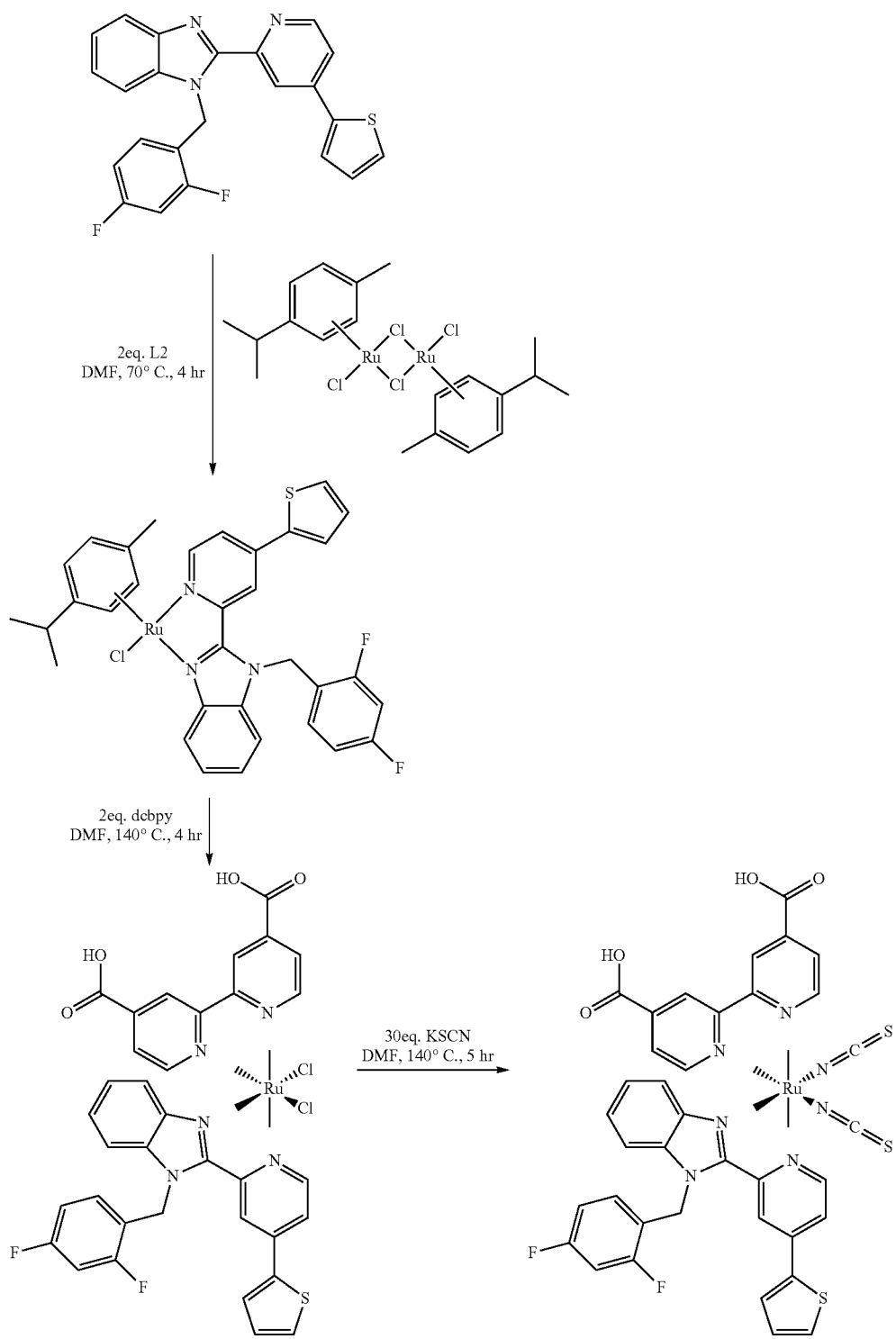

The steps of synthesis of ruthenium complex photosensitizer dye 2 are shown below.
 (1) In the environment of DMF and argon, two equivalents of the ligand L2 (about 0.322 g, about 0.8 mmol) are reacted with one equivalent of [RuCl$_2$(p-cymene)]$_2$ (about 0.244 g, about 0.4 mmol) at a temperature of about 70° C. for 4 hours to fog in [Ru(L2)(p-cymene)]Cl coordination from broken dichloride-bridged structure.
 (2) Then add two equivalents of 4,4'-dicarboxy-2,2'-bipyridine (dcbpy, L) (about 0.195 g, about 0.8 mmol) and raise the temperature to about 140° C. for reaction for about 4 hours, resulting in [Ru(L)(L2)(C1)$_2$].
 (3) Finally, add excessive amount of potassium thiocyanate (KSCN) into the mixture and let it react at about 140° C. for about 5 hours. After that, remove residual DMF in the reaction vessel using a distillation apparatus and KSCN residuals using water. After suction filtration, about 0.612 g of ruthenium complex photosensitizer dye 2 is obtained with the yield of about 88.5%.

Embodiments Number Three

1. The Synthesis of Ligands of Ruthenium Complex Photosensitizer Dye 3
Step 1

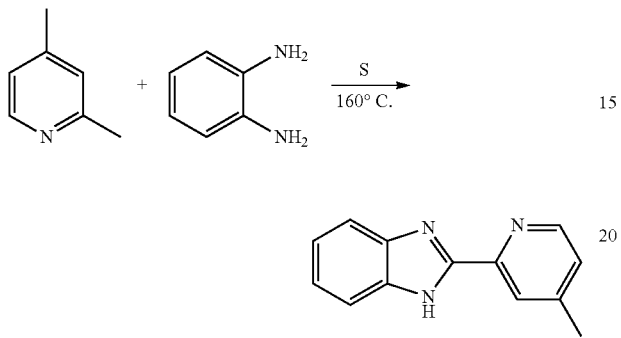

Mix about 0.96 g (about 0.03 mol) of sulfur (S) powder, about 1.07 g (about 0.01 mol) of 2,4-lutidine, and about 1.08 g (about 0.01 mol) of o-phenylenediamine in a single-necked flask. Then, raise the reaction temperature to about 160° C. and keep stirring evenly for about 6 hours till the yellow brown liquid turn into yellow solid. Finally, the reaction is terminated by addition of methanol. After filtering out the sulfur powder, the collected liquid is evaporated by a rotary concentrator. About 1.3 g of light yellow color solid is obtained with the yield of about 62.2%. The light yellow solid is 2-(4-methylpyridin-2-yl)benzimidazole.

Step 2

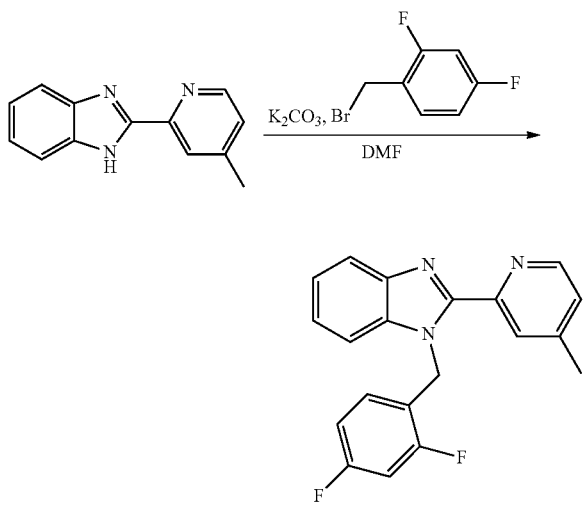

Mix about 0.209 g (about 1 mmol) of the light yellow solid product obtained in Step 1, about 0.276 g (about 2 mmol) of $K_2CO_3$, and about 15 mL of DMF in a reaction vessel and keep stirring for about 10 minutes. Then, carefully inject about 0.385 mL (about 3 mmol) of 2,4-difluorobenzyl bromide into the mixture by a syringe, and let it react for about 3 hours at room temperature. When the reaction ends, pour the mixture into iced water then extracte using EA. Collect and dehydrate the organic layer using anhydrous sodium sulfate. After filtration and concentration, a yellow color viscous liquid is obtained. Purify the yellow viscous liquid by column chromatograph using a hexane/EA solution (4:1) as eluent. Then, after vacuum suction, about 0.23 g of beige-white color solid is obtained with the yield of about 68.7%. The beige-white solid product is 1-(2,4-difluorobenzyl)-2-(4-methylpyridin-2-yl)benzimidazole.

Step 3

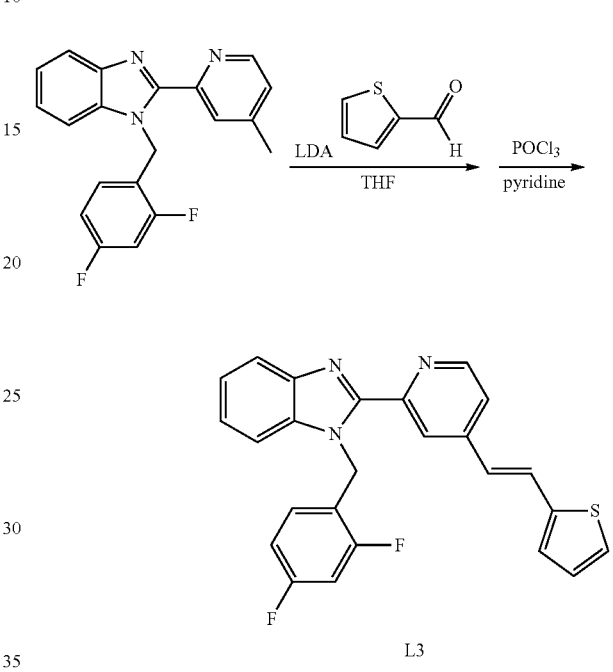

Put about 0.335 g (about 0.001 mmol) of the beige-white solid product obtained in Step 2 in a 100 mL double-necked flask. Then, the flask is alternately evacuated then filled with nitrogen gas for three times. After that, add 10 mL of anhydrous THF into the flask. Then slowly add 2M lithium diisopropylamide (LDA, about 0.0012 mol, about 0.6 mL) at a temperature of −20° C. Keep stirring the mixture for about 30 minutes at above temperature. Add about 0.17 g (about 0.0015 mol) of thiophene-2-carbaldehyde dissolved in anhydrous THF into the flask. Keep stirring the mixture for about 10 minutes at above temperature then move to room temperature for reaction for about 2 hours. The reaction is terminated by addition of methanol (MeOH). Next, after THF is removed, the residue was extracted three times using $CH_2Cl_2$. Collect and dehydrate the organic layer using anhydrous magnesium sulfate. After filtration and concentration, about 0.172 g of light yellow color viscous liquid is obtained. Place the light yellow viscous liquid in a 100 mL single-necked flask then add about 10 mL of pyridine. Under ice bath condition, add $POCl_3$ (about 0.0012 mol/0.11 mL). Then put the mixture in room temperature for reaction for about 10 minutes. Terminate the reaction by adding MeOH. Next, after pyridine was removed, the residue was extracted three times using $CH_2Cl_2$ (about 10 mL) and saline water. Collect and dehydrate the organic layer using anhydrous magnesium sulfate. Then, after vacuum suction, a yellow color liquid is obtained. Purify the yellow liquid by column chromatograph using a hexane/EA solution (2:1) as eluent. About 0.17 g of beige-white color solid (i.e. the ligands L3) is obtained with the yield of about 39.6%.

2. The Synthesis of Ruthenium Complex Photosensitizer
Dye 3
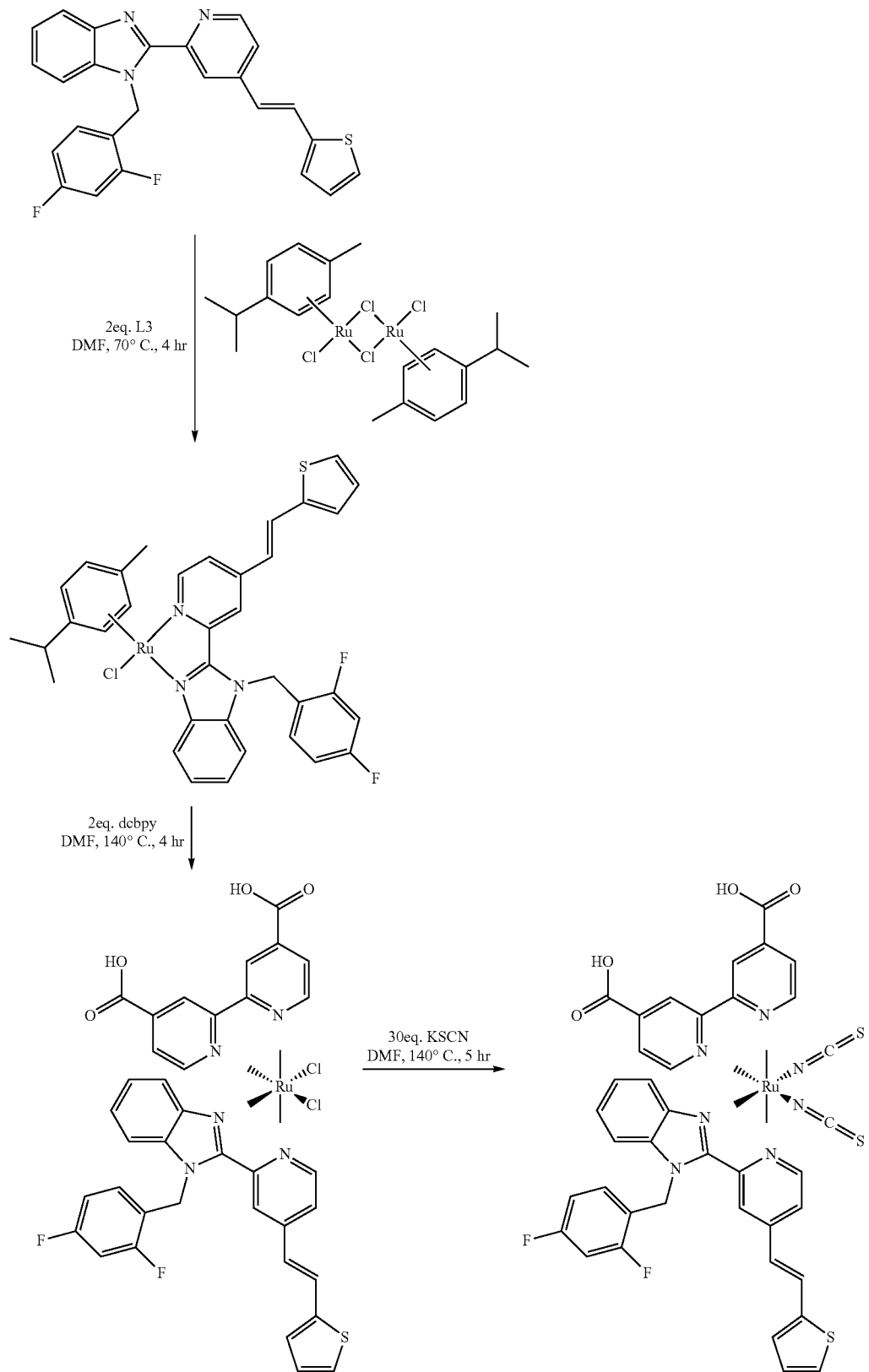

The steps of synthesis of ruthenium complex photosensitizer dye 3 are shown below.

(1) In the environment of DMF and argon, two equivalents of the ligand L3 (about 0.343 g, about 0.8 mmol) is reacted with one equivalent of [RuCl$_2$(p-cymene)]$_2$ (about 0.244 g, about 0.4 mmol) at a temperature of about 70° C. for about 4 hours to form [Ru(L3)(p-cymene)]Cl coordination . from the broken dichloride-bridged structure.

(2) Then add two equivalents of 4,4'-dicarboxy-2,2'-bipyridine (dcbpy, L) (about 0.195 g, about 0.8 mmol) to the mixture and raise the temperature to 140° C. for reaction for about 4 hours, resulting in [Ru(L)(L3)(Cl)$_2$].

(3) Finally, add excessive amount of KSCN to the mixture and let react at about 140° C. for about 5 hours. After that, remove residual DMF in the reaction vessel using a distillation apparatus and residuals of KSCN using water. After suction filtration, about 0.586 g of ruthenium complex photosensitizer dye 3 is obtained with the yield of about 82.3%.

FIG. 1 shows the comparison of UV-visible spectra of ruthenium complex photosensitizer dyes 1, 2 and 3 of this invention and conventional N719 dye.

Figure 2:
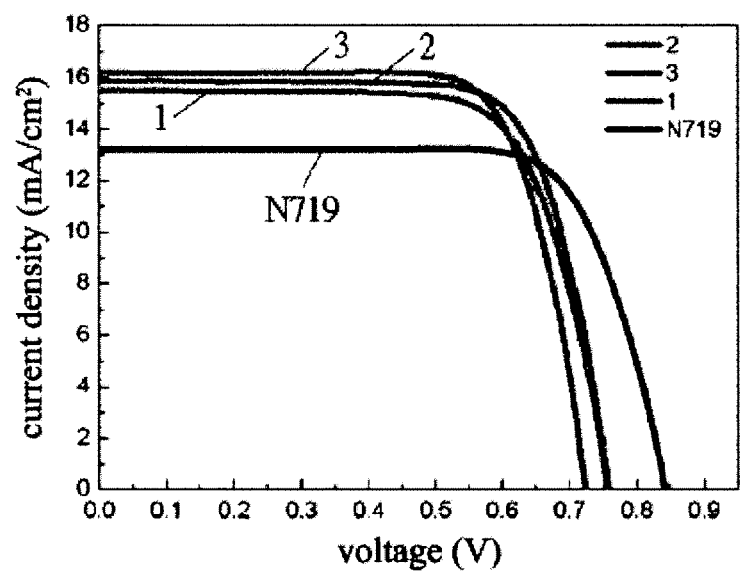
FIG. 2 shows the IV curves of the ruthenium complex photosensitizer dyes 1, 2 and 3 of this invention and the conventional N719 dye.

FIG. 2 shows the comparison of IV curves of the ruthenium complex photosensitizer dyes 1, 2 and 3 of this invention and conventional N719 dye.

Table 1 shows the comparison of photoelectric conversion efficiency of solar cell devices employing above-mentioned ruthenium complex photosensitizer dyes 1, 2 and 3 and conventional N719 dye. As shown the efficiency of the ruthenium complex photosensitizer dyes 1, 2 and 3 are better than that of the conventional N719 dye. The photoelectric conversion efficiency ($\eta$) is obtained by the equation below, $$\eta = \frac{P_{mp}}{P_{in}} = \frac{J_{mp} * V_{mp}}{P_{in}} = \frac{J_{SC} * V_{OC} * FF}{P_{in}}$$

where $P_{in}$ is the input radiation power, and $P_{mp}$ is the maximum output power ($=J_{mp} \times V_{mp}$), and FF stands for the fill factor defined as $$FF = \frac{J_{mp} * V_{mp}}{J_{SC} * V_{OC}}$$

where $L_{sc}$ is the short circuit current, and $V_\infty$ is the open circuit voltage.

TABLE 1

| Dye | $V_{oc}$ (V) | $J_{sc}$ (mA·cm$^{-2}$) | FF | $\eta$ (%) |
|---|---|---|---|---|
| 1 | 0.760 | 15.490 | 71.84 | 8.46 |
| 2 | 0.762 | 15.774 | 74.37 | 8.94 |
| 3 | 0.730 | 16.116 | 74.31 | 8.73 |
| N719 | 0.842 | 13.193 | 74.64 | 8.29 |

Since the ruthenium complex photosensitizer dyes of this invention have smaller molecular structures than the conventional N719 photosensitizer dye, they can be adsorbed, in greater amount, on thin titanium dioxide photoanodes of solar cells, leading to larger photoelectric current. Therefore, the layers of the titanium dioxide photoanodes can be reduced thus simplifying the processes and lowering the cost of manufacturing of the elements. Since the dye-sensitized solar cells employing the ruthenium complex photosensitizer dyes of this invention have higher photocurrent density than those using conventional N719 photosensitizer dye, the former has superior overall solar elements efficiency than the latter.

Although some embodiments of this invention are described in details above, it is intended that the scope of this invention may not be limited by the descriptions above, but rather by the claims appended hereto. Also, it is intended that the following appended claims be interpreted as that all possible alterations, pemiutations, and equivalents fall within the true spirit and scope of this invention.

What is claimed is:

1. A ruthenium complex photosensitizer dye for dye-sensitized solar cells, the ruthenium complex photosensitizer dye having the following general formula (I):

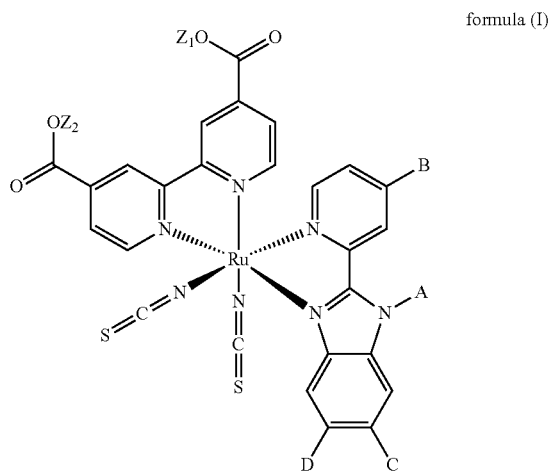

formula (I)

where $Z_1$ and $Z_2$ individually represent H, Li, Na, or tetraalkyl ammonium group represented by formula (a),

(a)

In formula (a), $X_1$ to $X_4$ individually represent $C_m H_{2m+1}$ (m is an integer from 1 to 6), In formula (I), A is one of the followings:

H, or $C_m H_{2m+1}$ (m is an integer from 1 to 15), or $CH_2[OC_2H_4]_pOC_mH_{2m+1}$ (p is an integer from 1 to 30, m is an integer from 1 to 15);

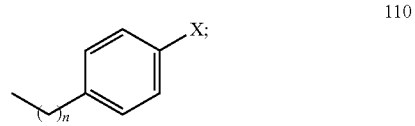

110

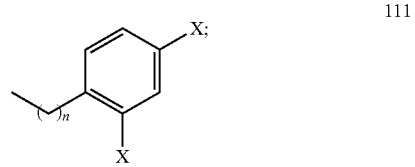

111

112 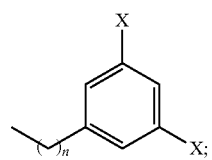
113 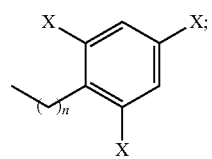
114 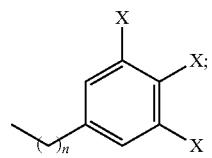
115 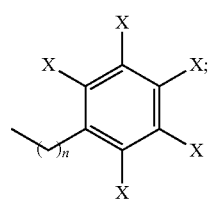
116 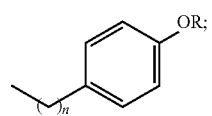
117 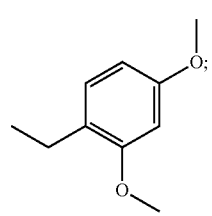
118 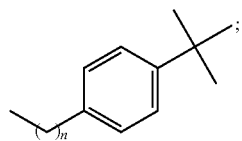
119 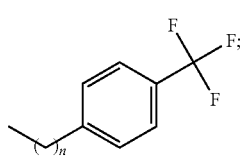
120 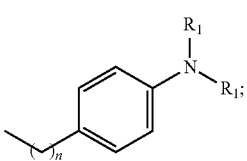
121 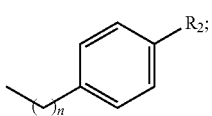
122 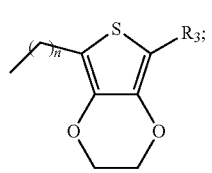
123 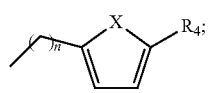
124 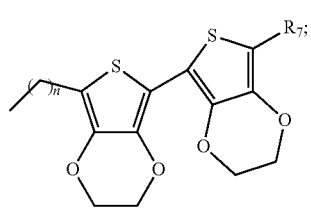
125 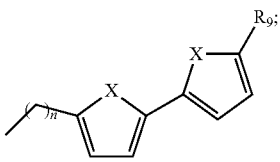
126 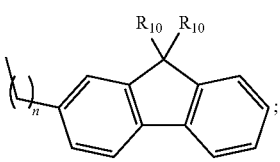
127 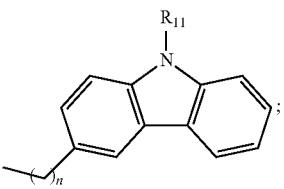
128

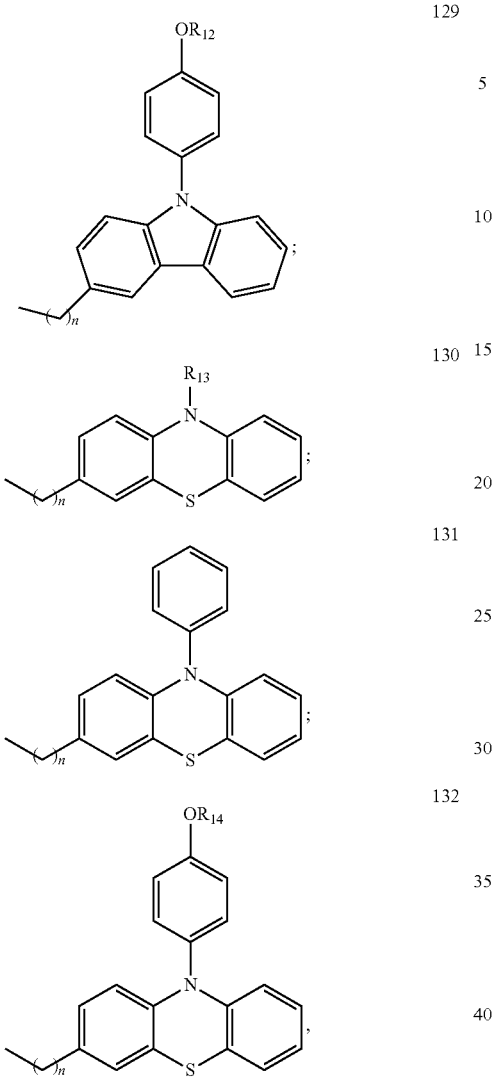
In formulae (110) to (132), n is zero or an integer from 1 to 15;
In formula (1), B, C, and D are individually selected from the followings: H, or $C_mH_{2m+1}$ (m is an integer from 1 to 15), or $CH_2[OC_2H_4]_pOC_mH_{2m+1}$ (p is an integer from 1 to 30, m is an integer from 1 to 15);
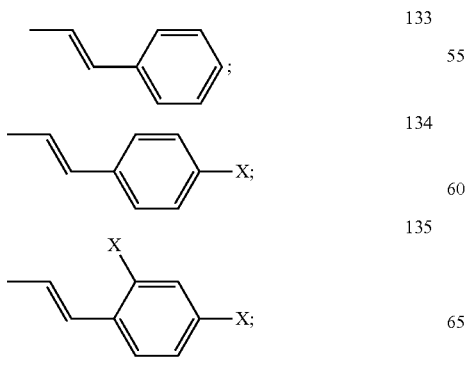
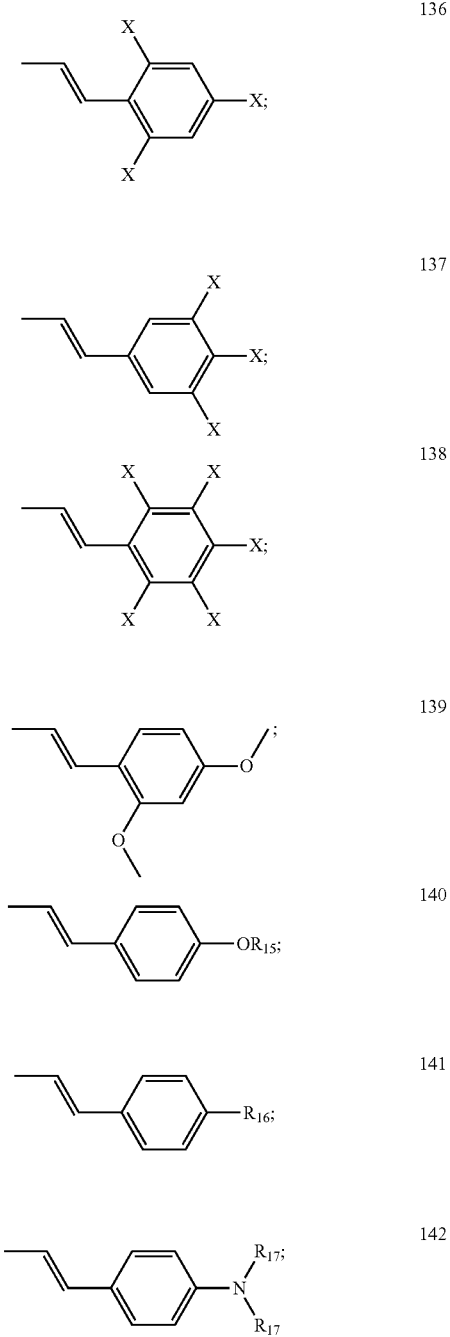
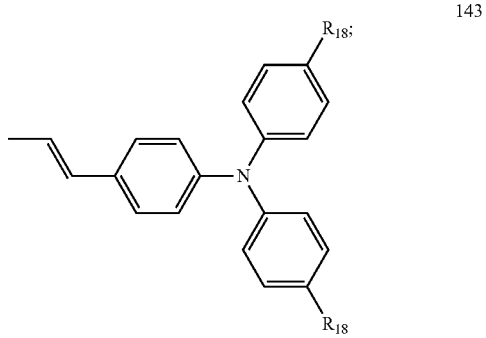

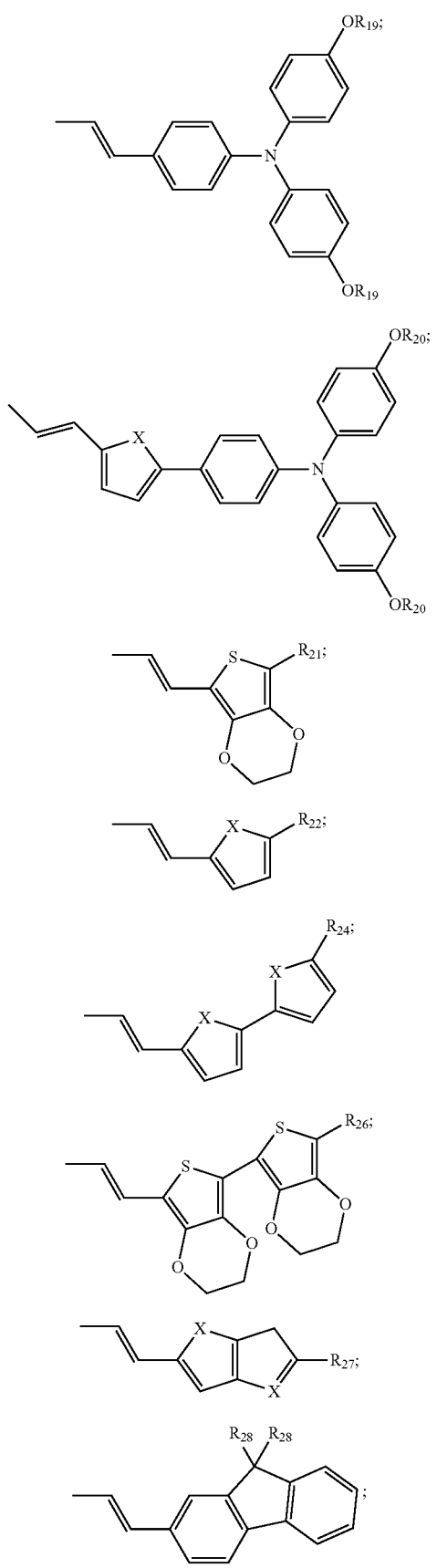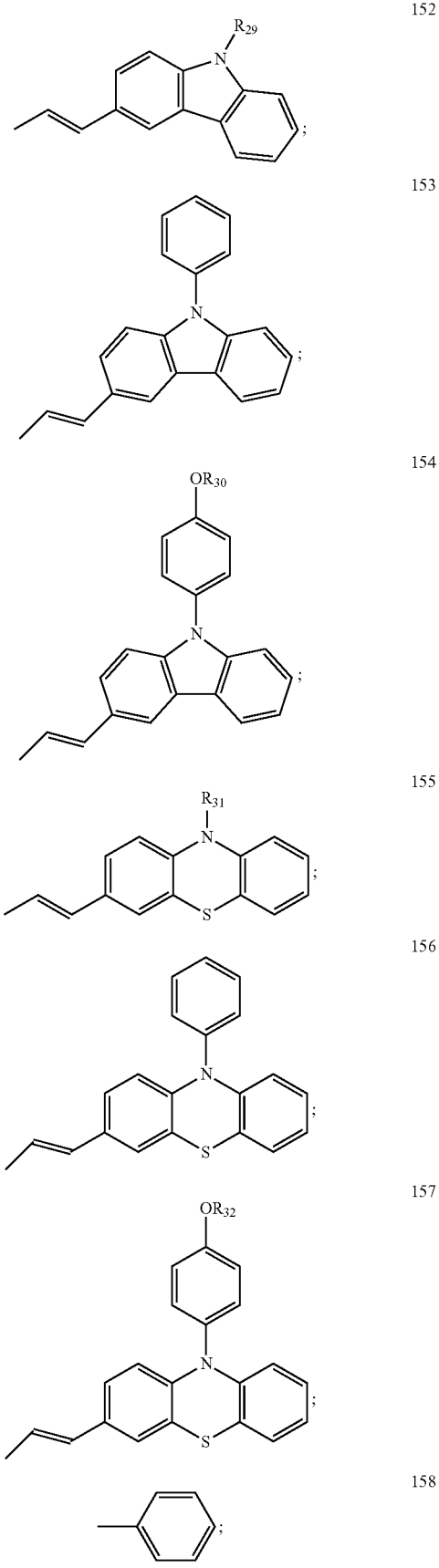

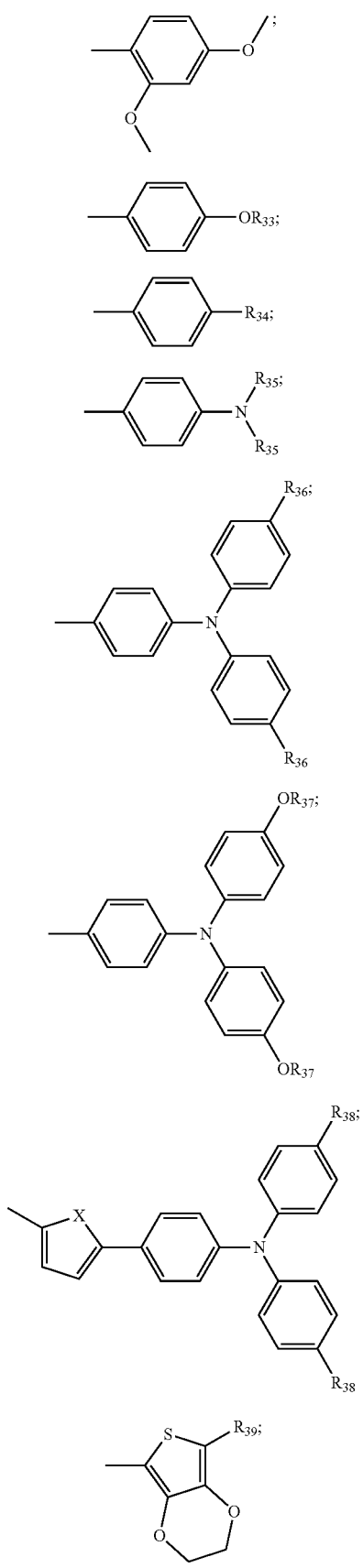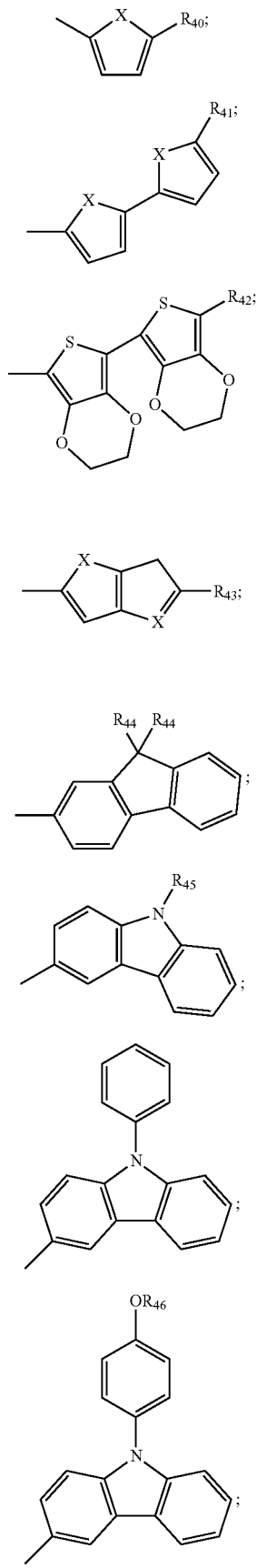

-continued

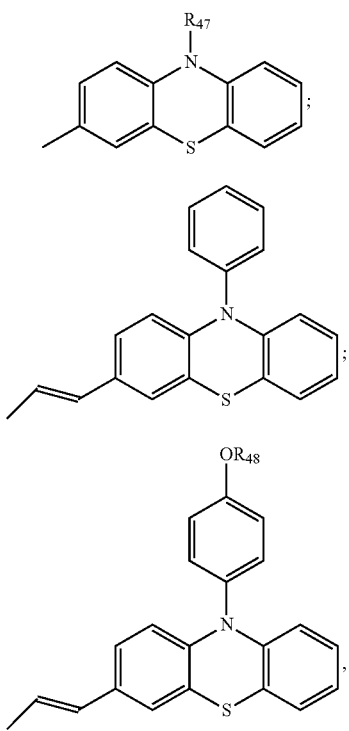

where $R_3, R_4, R_7, R_9, R_{10}, R_{21}, R_{22}, R_{24}, R_{26}, R_{27}$, and $R_{39}$ to $R_{43}$ represent $C_mH_{2m+1}$ (m is zero or an integer from 1 to 15), R, $R_{12}$ to $R_{15}, R_{19}, R_{28}$ to $R_{33}, R_{37}$, and $R_{44}$ to $R_{48}$ represent $C_mH_{2m+1}$ (m is an integer from 1 to 15), $R_1, R_{11}, R_{17}$, and $R_{35}$ represent $C_mH_{2m+1}$ (m is an integer from 1 to 15) or phenyl, $R_2, R_{16}$, and $R_{34}$ represent $CH_2[OC_2H_4]_pOC_mH_{2m+1}$ (p is an integer from 1 to 30, m is an integer from 1 to 15), $R_{18}, R_{36}$, and $R_{38}$ represent $CH_2[OC_2H_4]_pOC_mH_{m2+1}$ or $C_mH_{2m+1}$ (p is an integer from 1 to 30, in is an integer from 1 to 15);

In formulae 123, 125, 147, 148, 150, 170, 172, 173 and 175, X represents Se, S or O; in formulae 110 to 112, 114, 115 and 134 to 138, X represents F, Cl, Br, I or $C_mH_{2m+1}$ (m is an integer from 1 to 15); and in formulae 113, X represents F, Cl, Br, or I;

with the provision that at least one of $Z_1, Z_2$, B, C and D is not H.

2. The ruthenium complex photosensitizer dye of claim 1, where $Z_1$ and $Z_2$ Represent H.

3. The ruthenium complex photosensitizer dye of claim 2, where A is represented by the formula (111).

4. The ruthenium complex photosensitizer dye of claim 3, in formula (111), X represents F and n is equal to 1.

5. The ruthenium complex photosensitizer dye of claim 4, where C and D represent H.

6. The ruthenium complex photosensitizer dye of claim 5, where B is represented by the formula (147).

7. The ruthenium complex photosensitizer dye of claim 6, in formula (147), X represents S and $R_{22}$ represents H.

8. The ruthenium complex photosensitizer dye of claim 5, where B is represented by the formula (172).

9. The ruthenium complex photosensitizer dye of claim 8, in formula (172), X represents S and $R_{40}$ represents H.

* * * * *